(12) United States Patent
Katsuki et al.

(10) Patent No.: US 7,028,530 B2
(45) Date of Patent: Apr. 18, 2006

(54) GAS DETECTOR

(75) Inventors: Nobuharu Katsuki, Kyotanabe (JP); Rihito Shoji, Kadoma (JP); Masaki Tada, Neyagawa (JP); Junichi Yukawa, Osaka (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 130 days.

(21) Appl. No.: 10/502,223

(22) PCT Filed: Nov. 20, 2003

(86) PCT No.: PCT/JP03/14849

§ 371 (c)(1),
(2), (4) Date: Jul. 22, 2004

(87) PCT Pub. No.: WO2004/046706

PCT Pub. Date: Jun. 3, 2004

(65) Prior Publication Data

US 2005/0066707 A1 Mar. 31, 2005

(30) Foreign Application Priority Data

Nov. 21, 2002 (JP) ............................. 2002-337684

(51) Int. Cl.
*G01N 27/18* (2006.01)
(52) U.S. Cl. .................... 73/25.03; 73/25.04
(58) Field of Classification Search ............. 73/25.03, 73/29.02, 335.02, 25.04, 31.07
See application file for complete search history.

(56) References Cited

U.S. PATENT DOCUMENTS

| 3,429,178 | A | * | 2/1969 | Durbin | 73/23.21 |
| 4,399,684 | A | * | 8/1983 | Advani et al. | 73/25.03 |
| 4,896,143 | A | * | 1/1990 | Dolnick et al. | 340/634 |
| 4,928,513 | A | * | 5/1990 | Sugihara et al. | 73/25.03 |
| 5,297,419 | A | * | 3/1994 | Richardson | 73/25.03 |
| 5,551,283 | A | * | 9/1996 | Manaka et al. | 73/31.01 |
| 5,856,780 | A | * | 1/1999 | McGeehin | 340/540 |
| 6,840,103 | B1 | * | 1/2005 | Lee et al. | 73/335.05 |

FOREIGN PATENT DOCUMENTS

| JP | 56-148047 | 11/1981 |
| JP | 62-12861 | 1/1987 |
| JP | 04-291141 | 10/1992 |
| JP | 07-055748 | 3/1995 |
| JP | 08-184576 | 7/1996 |
| JP | 2001-124716 | 5/2001 |
| JP | 2001-141682 A | 5/2001 |

OTHER PUBLICATIONS

International Search Report for application No. PCT/JP03/14849 dated Feb. 3, 2004.

* cited by examiner

*Primary Examiner*—Michael Cygan
(74) *Attorney, Agent, or Firm*—RatnerPrestia

(57) ABSTRACT

There is provided a gas detector capable of detecting hydrogen concentration and humidity independently in the environment containing both hydrogen and water vapor. The gas detector comprises a high-temp exothermic detector unit and a low-temp exothermic detector unit provided with themosensitive resistors of different self-heating temperatures. The gas detector converts gas-level outputs produced by the high-temp exothermic detector unit and the low-temp exothermic detector unit responsive to the hydrogen concentration and humidity into electric signals, and outputs them after computing electrically levels of the hydrogen concentration and humidity contained in a gas introduced into the two detector units through a gas intake opening.

15 Claims, 11 Drawing Sheets

GAS DETECTOR

This application is a U.S. National Phase application of PCT International application PCT/JP2003/014849.

TECHNICAL FIELD

The present invention relates to a gas detector for detecting hydrogen leakage and humidity.

BACKGROUND ART

There are intense activities in recent years for development of fuel cells that generate electric power from hydrogen and oxygen in the air. These activities are motivated by three reasons below.

First, they are excellent power generating methods in view of the environmental protection, because substance being released during generation of electricity is only water. Secondly, they save energy because they are fundamentally superior in efficiency of generating the electric energy. Thirdly, they have an advantage of using even thermal energy by collecting heat produced during generation of electricity. They therefore hold expectation as the last resort to solve the energy and environmental problems in the global scale.

Such fuel cell systems as discussed above are considered useful for application to home-use cogeneration systems as well as automobiles.

The fuel cell systems are expected to grow more and more in the future as alternative sources of energy to replace the existing thermal power generation and gasoline engines that use fossil fuel. Because the fuel cells use hydrogen for the fuel, it is important that they are provided with safety measures. In other words, it is indispensable for the fuel cells to be equipped with hydrogen concentration detectors for detecting leakage of hydrogen to ensure the safety. There have been hitherto proposed some devices as such hydrogen concentration detectors that detect hydrogen concentration by monitoring temperature change of heater elements based on the principle that a coefficient of thermal conductivity of hydrogen is extremely large as compared to other gases. When hydrogen gas reaches a heater element which is in a state of thermal equilibrium in the air, for instance, there occurs a change in amount of heat being taken away from the heater element, and causes it to lose the thermal equilibrium. As a result, temperature of the heater element changes according to a level of the hydrogen concentration. The hydrogen concentration detector uses a temperature sensor element to electrically detect this temperature change. Platinum temperature-measuring elements are well known as the heater elements, and the temperature sensor elements used for such hydrogen concentration detectors. Since platinum has a relatively high specific resistance among metals, it generates heat in itself when an electric current is fed through. In addition, because platinum also has a relatively high temperature coefficient of resistance among metals, it can be used for detection of temperature change corresponding to the hydrogen concentration through a change in resistance. A gas detector contrived to use the above method is disclosed in the official publication of unexamined Japanese utility model, No. S62-12861. It uses two detectors of different heating temperatures, and a factor multiplier and an arithmetic unit to solve a set of simultaneous equations obtained from outputs of the two detectors. This gas detector can thus measure a level of concentration of the gas to be detected while eliminating influence of interfering gases.

However, the above gas detector of the prior art shows a drawback when there is water vapor present as an interfering gas in the gas to be detected. In other words, a resistance of platinum changes precisely in proportion to the level of hydrogen concentration only if there is no water vapor. However, the water vapor, if present, also changes the resistance of platinum. As a result, the gas detector is unable to determine what has caused the change in resistance, whether it is due to hydrogen, water vapor, or both of them in coexistence. It is for this reason to solve the above problem that the gas detector of the prior art makes arithmetic operation of the simultaneous equations to eliminate influence of the interfering gases. However, water vapor shows such characteristics that its coefficient of thermal conductivity rises with increase in absolute humidity, but start descending once the coefficient value reaches a peak level in an atmosphere in which the water vapor having polarities is mixed with unpolarized air, hydrogen and the like, although the coefficient value of water vapor is extremely smaller than that of hydrogen when present separately.

Therefore, in the case where a large amount of water vapor is assumed present in relation to hydrogen, a coefficient of thermal conductivity in the mixture of the water vapor and hydrogen rises once with increase in absolute humidity and descends after it reaches the peak level, as previously stated, when detecting hydrogen leakage. That is, the mixture shows a characteristic that the coefficient of thermal conductivity changes in a form of quadratic curve. Therefore, if a gas detector is adapted to use the prior art technique of solving the simultaneous equations as described above, it calculates only a level of hydrogen through arithmetic operation of the simultaneous equations in two unknowns, and has the following problems. That is, the operation is very complex as a signal processing technique of the sensor, and it gives rise to problems with regard to detecting accuracy, multiplicity of uses, cost of putting it to practical use, and so forth.

Accordingly, it is an object of the present invention to provide a gas detector having a capability of detecting hydrogen concentration by distinguishing it from moisture in the environment wherein the hydrogen coexists with water vapor.

SUMMARY OF THE INVENTION

There is provided a gas detector comprising: a high-temp exothermic detector unit having a high-temp exothermic gas sensor element and a high-temp exothermic temperature sensor element, each made of a resistor of which a resistance changes responsive to temperature, the high-temp exothermic gas sensor element exposed to a gas being detected, and the high-temp exothermic temperature sensor element sealed in an unperforated casing filled with dry air and maintained to generate heat to a temperature substantially equal to a self-heating temperature of the high-temp exothermic gas sensor element as measured in dry air; and a low-temp exothermic detector unit having a low-temp exothermic gas sensor element and a low-temp exothermic temperature sensor element, each made of a resistor of which a resistance changes responsive to temperature, the low-temp exothermic gas sensor element exposed to the gas being detected, and the low-temp exothermic temperature sensor element sealed in another unperforated casing filled with dry air and maintained to generate heat to a temperature substantially equal to a self-heating temperature of the low-temp exothermic gas sensor element as measured in dry air, wherein the self-heating temperature of the high-temp exothermic gas sensor element and the high-temp exothermic temperature sensor element of the high-temp exothermic detector unit is set to be different from the self-heating temperature of the low-temp exothermic gas sensor element and the low-temp exothermic temperature sensor element of the low-temp exothermic detector unit as measured in the dry air. The gas detector performs processes of: converting resistance values of the individual gas sensor elements that change responsive to hydrogen concentration, humidity and an ambient temperature, and resistance values of the individual temperature sensor elements that change responsive to the ambient temperature into electrical gas-level outputs corresponding to the hydrogen concentration and the humidity; normalizing the gas-level outputs gained from the individual detector units by using a hydrogen sensitivity conversion factor obtained under a known level of hydrogen concentration; obtaining a humidity-level output derived as a difference between the normalized outputs; and producing outputs representing levels of the hydrogen concentration and the humidity by correcting the normalized outputs with a humidity-level correction formula established through a correlation of a humidity-level correction value obtained from the humidity-level output gained under an environment of known humidity level and the individual normalized outputs responsive to the humidity.

DETAILED DESCRIPTION OF PREFERRED EMBODIMENTS

Referring to the accompanying drawings, description is provided hereinafter of the exemplary embodiments of the present invention.

The drawings are intended to schematically show only positions of individual elements, and they therefore do not reflect their dimensions accurately. In the present invention, a high-temp exothermic gas sensor element (hereinafter referred to as "GDH") defines a gas sensor element that generates heat by itself to maintain it in a state of high temperature for the proper function as a sensor element.

In addition, a low-temp exothermic gas sensor element (hereinafter referred to as "GDL") defines another gas sensor element that generates heat by itself to maintain it at a temperature lower than that of the GDH.

It is desirable that these two temperatures differ by 10° C. or greater, but a difference of about 50° C. is more desirable.

Likewise, a high-temp exothermic temperature sensor element (referred to as "TDH") defines a temperature sensor element that generates heat by itself to maintain it in a state of high temperature for the proper function as a sensor element. Also, a low-temp exothermic temperature sensor element (referred to as "TDL") defines another temperature sensor element that generates heat by itself to maintain it at a temperature lower than that of the TDH. It is also desirable that these two temperatures differ by 10° C. or greater, but a difference of about 50° C. is more desirable. It is desirable in addition that the low temperature maintained by the GDL and TDL is 100° C. or higher.

Furthermore, a high-temp exothermic detector unit (referred to as "DPH") comprises the GDH and the TDH, and it additionally includes a circuit for operating them.

Similarly, a low-temp exothermic detector unit (referred to as "DPL") comprises the GDL and the TDL, and includes a circuit for operating them.

(First Exemplary Embodiment)

Figure 1A:
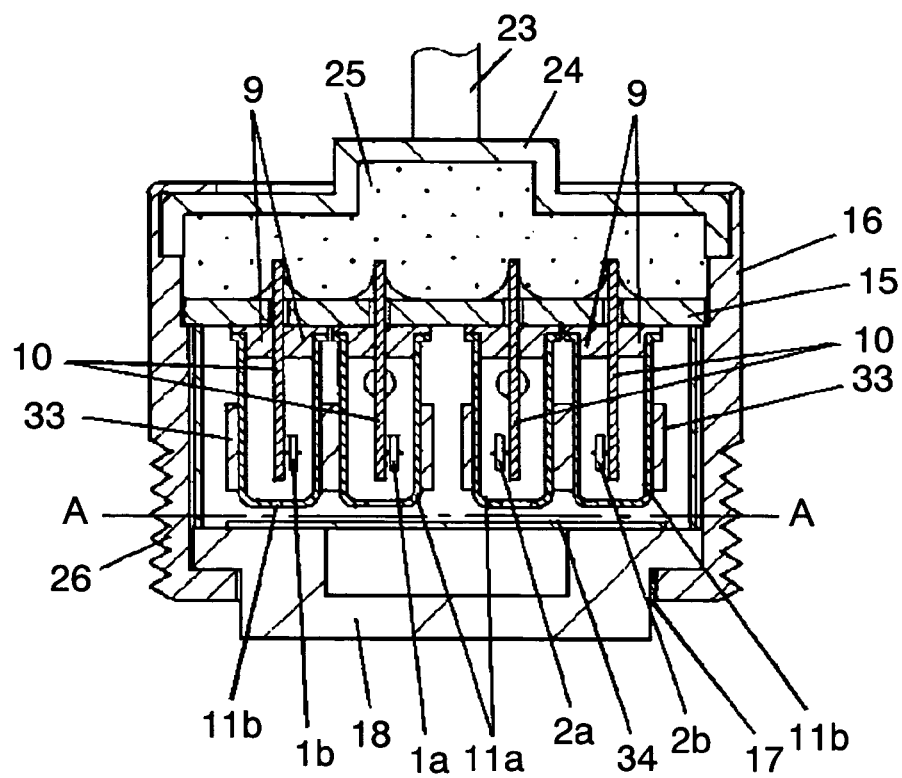
FIG. 1A is a cross sectional view showing a structure of a gas detector according to a first exemplary embodiment of the present invention.
Figure 2:
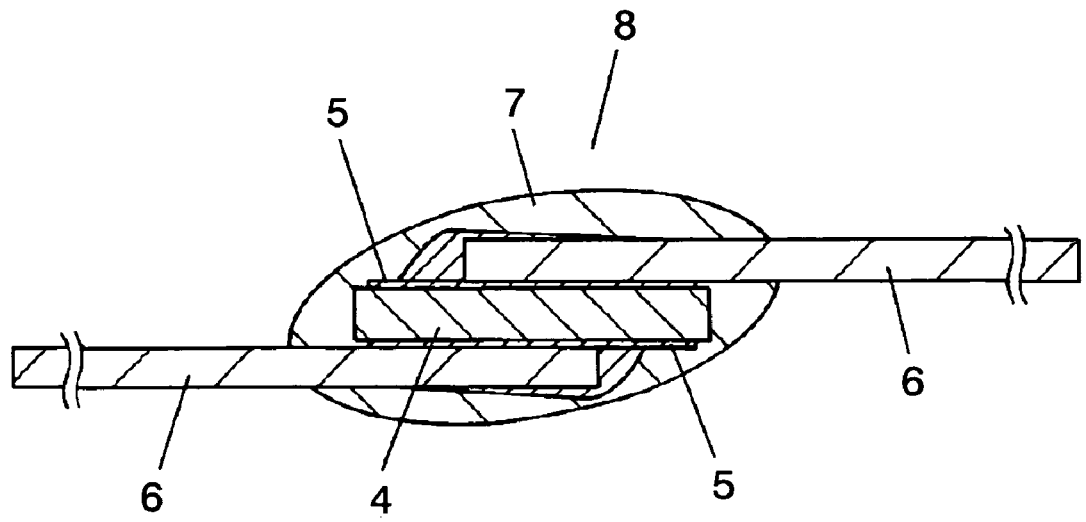
FIG. 2 is a longitudinally sectioned view of a thermistor used in the gas detector according to the first exemplary embodiment of this invention.

FIG. 1A shows GDH 1a, TDH 1b, GDL 2a and TDL 2b. Each of these elements is composed of a thermistor, of which a structure is shown in FIG. 2. Heat generating resistors of any kind can be used as these elements, if resistances are variable responsive to temperature change. Thermistor element 4 used here is made of a sintered oxide compound composed of manganese, cobalt, copper and vanadium, which is cut into a disc-like shape of 1.2 mm in diameter and 0.2 mm in thickness. B-constant defining a temperature characteristic of it is 2,300K. However, any element having a value in a range of approximately 1,000 to 3,000K may also be used. Thermistor element 4 is provided with electrodes 5 formed on both surfaces thereof by printing and firing conductive paste of silver, palladium and platinum based material. Lead wires 6 made of a platinum wire of 0.15 mm in diameter are connected electrically and mechanically to the both electrodes 5 with the conductive paste. Glass layer 7 of a low melting point is formed to cover the entire exterior surface of thermistor element 4, including the electrodes 5 and parts of lead wires 6.

Glass layer 7 is formed by coating a pasty form glass powder having a firing temperature of 550° C. mixed with organic solvent.

Thermistor element 4 is concealed entirely in glass layer 7 to thus complete thermistor 8.

Thermistors 8 produced in the manner as described above are prepared here for a total of four pieces.

Figure 1B:
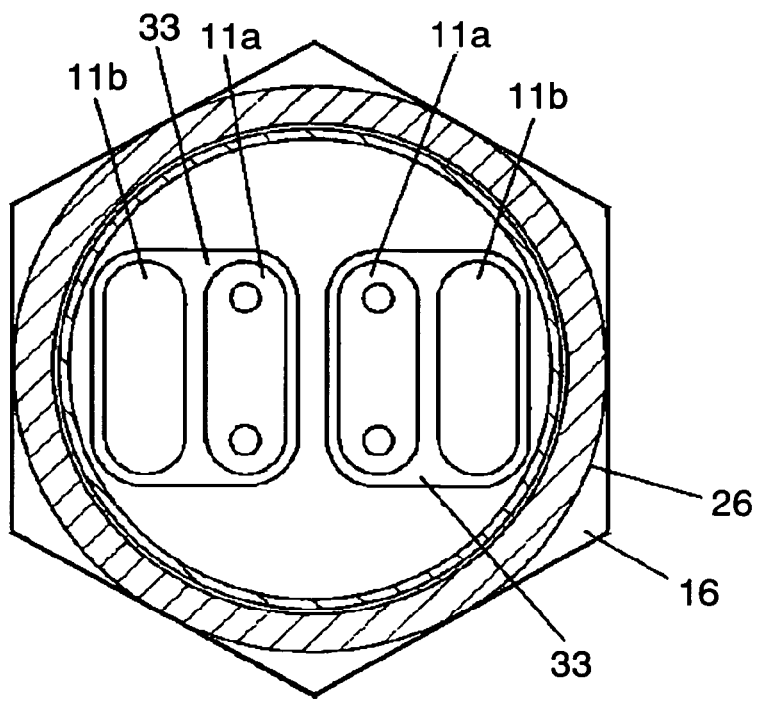
FIG. 1B is a laterally sectioned view taken along a line A—A of the gas detector according to the first exemplary embodiment of this invention.
Figure 3:
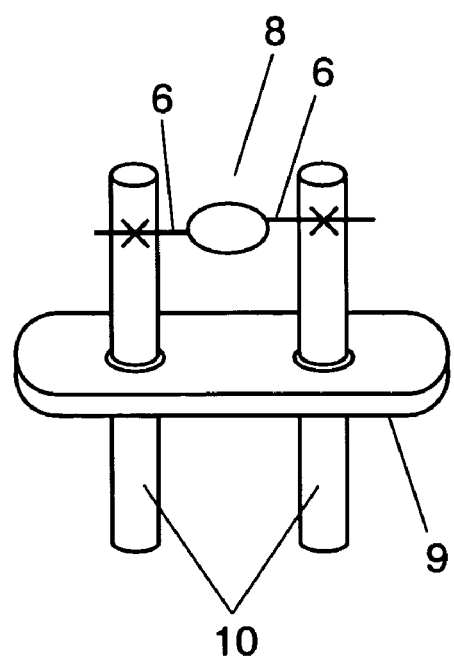
FIG. 3 is a perspective view illustrating a method of assembling a detector unit of the gas detector according to the first exemplary embodiment of this invention.

Next, electrical and mechanical connection of each thermistor 8 is made by resistance-welding lead wires 6 to pins 10 fixed to base 9, as shown in FIG. 3 (shown by marks "x" in the figure). The four pieces of assembled elements are used as GDH 1a, TDH 1b, GDL 2a and TDL 2b respectively. Each of TDH 1b and TDL 2b is enclosed in unperforated casing 11b in a space filled with dry air, as shown in FIG. 1A and FIG. 1B. The unperforated casing 11b and base 9 are bonded and sealed by projection welding.

The casing is formed of a metal. It is desirable to use stainless steel in the light of corrosion resistance and weldability.

TDH 1b and TDL 2b constructed as above output voltages across their end terminals corresponding to their respective temperatures inside the gas detector without being influenced by the gas to be detected. Each of GDH 1a and GDL 2a is covered with perforated casing 11a having through holes of 1.2 mm in diameter at four locations as shown in FIG. 1A. Perforated casing 11a and base 9 are bonded and sealed by projection welding.

In the structures including perforated casings 11a and unperforated casings 11b, the temperature sensor elements (TDH 1b and TDL 2b) and the gas sensor elements (GDH 1a and GDL 2a) are made to be equal in their thermal capacity, so that both of these sensor elements have generally equal heat generating characteristic.

Because of the above structures, the heat generating characteristic of TDH 1b becomes substantially equal to that of GDT 1a. In addition, the heat generating characteristic of TDL 2b also becomes substantially equal to that of GDL 2a. They can thus make an accurate temperature correction to the effect of ambient temperature. Furthermore, TDH 1b shows a temperature rise profile similar to that of GDH 1a during startup of the gas detector. TDL 2b also shows a temperature rise profile similar to that of GDL 2a.

High-speed startup of the gas detector can be made possible as a result of the above. GDL 2a enclosed in perforated casing 11a and TDL 2b enclosed in unperforated casing 11b are connected together with heat conductive plate 33 made of a material of high coefficient of thermal conductivity such as copper, aluminum and the like material. Likewise, GDH 1a enclosed in perforated casing 11a and TDH 1b enclosed in unperforated casing 11b are connected together with another heat conductive plate 33. Accordingly, the individual sensor elements are kept in a generally equal state of thermal conduction between perforated casings 11a and unperforated casings 11b provided around the sensor elements 1a, 1b, 2a and 2b and the surrounding environment.

This makes the gas detector capable of performing highly accurate detection even under transitional changes in the ambient temperature, in addition to achieving a good effect for quick startup. For GDH 1a, TDH 1b, GDL 2a and TDL 2b, pins 10 are connected electrically and mechanically at their one ends to circuit board 15 by soldering. They are then housed in container 16 having a hexagonal exterior as shown in FIG. 1B.

Flat heater 34 is placed in the vicinity of GDH 1a, TDH 1b, GDL 2a and TDL 2b as shown in FIG. 1A. Heater 34 is energized for about five seconds to a temperature of 200° C. immediately after the startup of the detector.

Operation of the heater 34 heats up thermistors 8 to thereby lower their resistances to such values that make self-heating possible even when the ambient temperature is so low that the resistances of thermistor elements 4 are substantially large. The detector can be thus made operative even in a low temperature. In the first exemplary embodiment here, although heater 34 is shown as being operated during every startup, it may be operated only when the ambient temperature is low. For this purpose, microcomputer 32 may be used to monitor any of resistances and voltage values of thermistors 8, and heater 34 is operated only when the temperature is determined low, or the resistances are high. This can also save power consumption.

Filter 18 made of a sintered metal is fitted in gas intake opening 17. Filter 18 has a circular shape, and it is disposed in a manner to project outward from container 16. When the gas to be detected contains moisture, there is a possibility that dew condensation occurs inside container 16 depending on the condition of ambient temperature.

Figure 4:
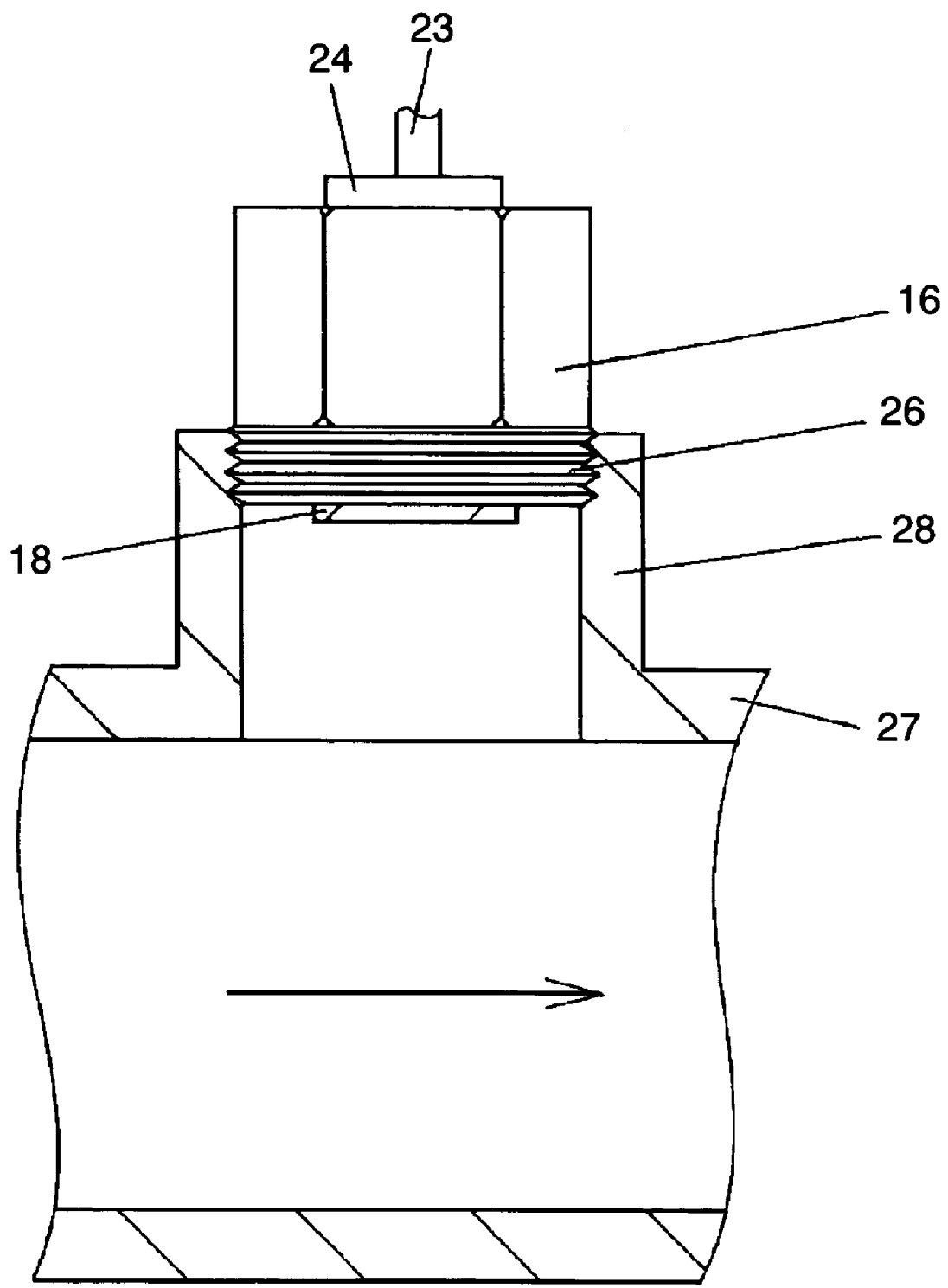
FIG. 4 is a cross sectional view illustrating an installation method of the gas detector to a pipe, according to the first exemplary embodiment of this invention.

The gas detector is therefore placed in such an orientation that gas intake opening 17 faces the direction of gravity, so as to let the condensed water flow out smoothly and drained to the outside of filter 18 by the gravity. Container cover 24 having conductor cable 23 disposed beforehand in a manner to pass through is placed above circuit board 15 inside container 16, and it is secured to container 16 by crimping. Furthermore, a space between circuit board 15 and container cover 24 is filled in its entirety with moisture resistant resin 25 injected through a filling opening (not shown in the figure) provided in container cover 24, and it is cured. The gas detector thus completed is fixed to a location where detection of gas concentration is desired, by tightening screw 26 formed on a peripheral portion of container 16. In the case of detecting gas concentration in a piping system, mounting hole 28 for the gas detector is formed in a part of pipe 27, as shown in FIG. 4. The gas detector is secured by tightening screw 26 into mounting hole 28. In this structure, since gas intake opening 17 is located away from the main gas stream inside pipe 27, an undesirable influence attributed by a flow speed of the main gas stream can be alleviated.

Description is provided next of an operation of the gas detector.

Figure 5:
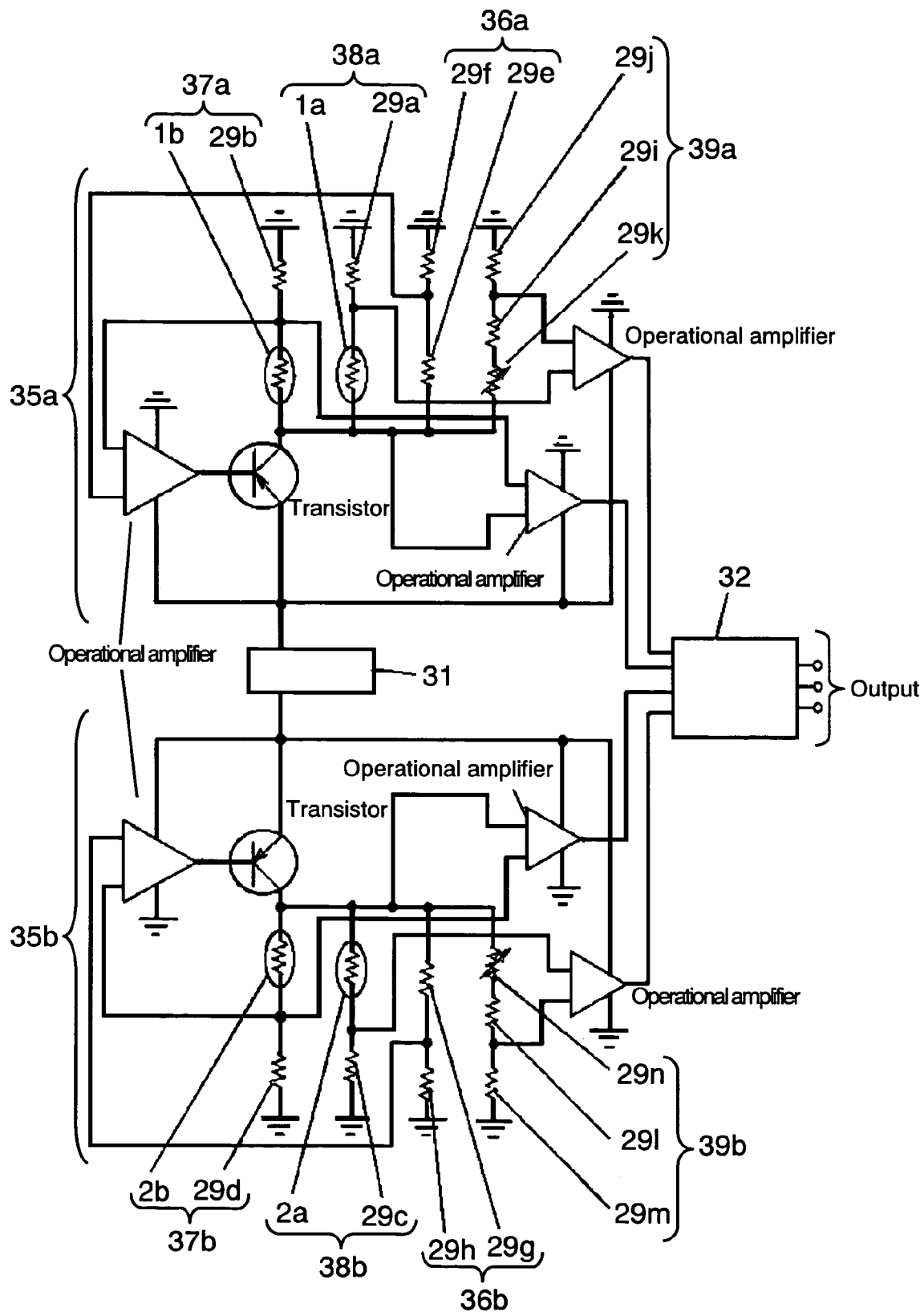
FIG. 5 is a diagram showing a circuit configuration of the gas detector according to the first exemplary embodiment of this invention.

As shown in FIG. 5, GDH 1a, TDH 1b, GDL 2a and TDL 2b are connected in series with fixed resistors 29a, 29b, 29c and 29d respectively. Here, fixed resistors 29a and 29b are of 220 Ω in resistance and fixed resistors 29c and 29d are of 500 Ω in resistance respectively. These resistors thus control the heating temperatures of GDH 1a and TDH 1b to approximately 190° C. and those of GDL 2a and TDL 2b to approximately 140° C. D.C. power source 31 is connected to these circuits and supplies electrical power of 15V.

Describing now pertains to a method of controlling the individual elements at constant heating temperatures. In this first exemplary embodiment, two sensor elements 1a and 1b of DPH 35a, and two sensor elements 2a and 2b of DPL 35b are so controlled that their heating temperatures when measured in dry air are kept constant irrespective of an influence of the ambient temperature.

The two sensor elements 1a and 1b of DPH 35a are controlled in a manner as described hereinafter to make their heating temperatures constant.

Element resistance regulating circuit 36a in DPH 35a consists of fixed resistor 29e of 11 kΩ and another fixed resistor 29*f* of 33 kΩ connected in series. A voltage across the both ends of fixed resistor 29*f* serves as a control voltage.

Ambient temperature detecting circuit 37*a* comprises fixed resistor 29*b* of 220 Ω connected in series to TDH 1*b*.

A voltage across the both ends of fixed resistor 29*b* is a to-be-controlled voltage. Here, a voltage applied to element resistance regulating circuit 36*a*, gas detecting circuit 38*a* comprising the series connection of GDH 1*a* and fixed resistor 29*a* of 220 Ω, reference voltage circuit 39*a* and ambient temperature detecting circuit 37*a* is regulated through an operational amplifier, a transistor and the like in response to changes in the ambient temperature, in a manner to equalize the to-be-controlled voltage with the control voltage.

Since the resistances of TDH 1*b* and GDH 1*a* are kept to be constant at all times as described above, the heating temperatures of them can be maintained constant.

On the other hand, heating temperatures of the elements at the side of DPL 35*b* are controlled constant in the following manner. Element resistance regulating circuit 36*b* in DPL 35*b* comprises fixed resistor 29*g* of 43 kΩ and another fixed resistor 29*h* of 100 kΩ connected in series.

A voltage across the both ends of fixed resistor 29*h* serves as a control voltage. Ambient temperature detecting circuit 37*b* comprises fixed resistor 29*d* of 500 Ω connected in series to TDL 2*b*. A voltage across the both ends of fixed resistor 29*d* is a to-be-controlled voltage. A voltage applied to element resistance regulating circuit 36*b*, gas detecting circuit 38*b* comprising the series connection of GDL 2*a* and fixed resistor 29*c* of 500 Ω, reference voltage circuit 39*b* and ambient temperature detecting circuit 37*b* is regulated through an operational amplifier, a transistor and the like in response to changes in the ambient temperature, in the manner as described above, to equalize the to-be-controlled voltage with the control voltage.

Since the resistances of TDL 2*b* and GDL 2*a* are kept to be constant at all the time as described, the heating temperatures of them can be controlled constant.

Accordingly, since the ambient temperatures of the individual sensor elements are kept generally uniform, they reduce changes in coefficient of thermal conductivity of the gas to be detected due to the effect of temperature. As a result, the gas detector can detect gas concentration with high accuracy.

This embodiment also provides an advantage of shortening a warm-up time because it controls the self-heating temperatures of the individual sensor elements constant immediately after the startup of the gas detector.

Describing next pertains to the steps of signal processing to obtain a gas-level output from each of the detector units.

In DPH 35*a*, signal processing is performed in the following manner to obtain a gas-level output. Reference voltage circuit 39*a* for producing a reference voltage comprises a series connection of fixed resistor 29*i* of a resistance value smaller than 11 kΩ, fixed resistor 29*j* of 33 kΩ and variable resistor 29*k*. A voltage across both ends of fixed resistor 29*j* is taken as the reference voltage. Gas detecting circuit 38*a* comprises fixed resistor 29*a* of 220 Ω connected in series to GDH 1*a*. A voltage across both ends of fixed resistor 29*a* is a gas-level output voltage, which is used in the signal processing to obtain a difference in voltage potential in comparison to the reference voltage. If there is a difference between the reference voltage and the gas-level output voltage in the air containing no hydrogen and humidity, a resistance of variable resistor 29*k* is adjusted to eliminate the difference.

Signal processing in DPL 35*b* is performed in the following manner to obtain a gas-level output. Reference voltage circuit 39*b* for producing another reference voltage comprises a series connection of fixed resistor 29*l* of a resistance value smaller than 43 kΩ, fixed resistor 29*m* of 100 kΩ, and variable resistor 29*n*. A voltage across both ends of fixed resistor 29*m* is used as the reference voltage.

Gas detecting circuit 38*b* comprises fixed resistor 29*c* of 500 Ω connected in series to GDL 2*a*. A voltage across both ends of fixed resistor 29*c* is a gas-level output voltage, which is used in the signal processing to obtain a difference in voltage potential in comparison to the reference voltage. If there is a difference between the reference voltage and the gas-level output voltage, a resistance of variable resistor 29*n* is adjusted to eliminate the difference in the like manner as above.

Accordingly, in the dry air containing no hydrogen and humidity, this embodiment can reduce variations in the potential differences between these reference voltages and gas-level output voltages attributable to the variations of the ambient temperature, and therefore it provides an advantage of making highly accurate detection.

The gas-level outputs of DPH 35*a* and DPL 35*b* obtained through the above signal processing and voltages appearing at both ends of temperature sensor elements 1*b* and 2*b* are input to microcomputer 32. Microcomputer 32 produces outputs corresponding to hydrogen concentration, humidity and temperature respectively by performing an operation which will be described later.

The gas to be detected in the vicinity of the gas detector, that is the gas inside the pipe, passes through filter 18 disposed to gas intake opening 17, and reaches GDH 1*a*, TDH 1*b*, GDL 2*a* and TDL 2*b*. GDH 1*a* and GDL 2*a* generate heat in themselves. If the gas being detected contains any of hydrogen and moisture, temperatures of GDH 1*a* and GDL 2*a* change because the hydrogen and moisture change the thermal conductivity of the gas being detected and amounts of the heat taken away from them depending on a level of the concentration.

On the other hand, structures of TDH 1*b* and TDL 2*b* are such that they are individually sealed inside unperforated casings 11*b* with dry air.

Therefore, both TDH 1*b* and TDL 2*b* produce output voltages at both ends thereof that correspond to the temperatures inside the gas detector, without being influenced by the gas to be detected. These changes are converted into gas-level outputs respectively by the above method of signal processing, and input to microcomputer 32.

In the first exemplary embodiment, thermistors 8 are used for sensor elements 1*a*, 1*b*, 2*a* and 2*b*, since they show a high level of sensitivity to hydrogen gas. However, because of the high sensitivity, thermistors 8, when used, are influenced considerably by the changes in the coefficient of thermal conductivity of hydrogen due to the ambient temperature. It is therefore necessary to make correction of the sensitivity to hydrogen concentration according to the ambient temperature. Since a hydrogen sensitivity conversion factor for each of the gas-level outputs is variable responsive to changes in the ambient temperature, the correction is made by using a sensitivity correction formula. The sensitivity correction formula is derived from a correlation between voltage outputs across the both ends of each of temperature sensor elements 1*b* and 2*b* and hydrogen sensitivity conversion factors under the environment of various ambient temperatures. For instance, gas-level outputs using a standard gas prepared by mixing 1% concentration of hydrogen in dry air, and voltages across the both ends of temperature sensor elements 1*b* and 2*b* are measured at temperatures of −40° C., 25° C. and 80° C. The gas-level outputs in the standard gas generally have a tendency to decrease with increase in the temperature, as opposed to the voltages across the both ends of temperature sensor elements 1*b* and 2*b*, which can be considered of nearly a linear correlation.

Therefore, the voltages at both ends of the temperature sensor elements 1*b* and 2*b* are also input to microcomputer 32.

Microcomputer 32 performs an arithmetic operation based on the individual gas-level outputs and the voltages at both ends of the temperature sensor elements 1*b* and 2*b*, and produces outputs corresponding to hydrogen concentration, humidity and temperature respectively.

Description will be provided next of the operation performed by microcomputer 32. First, a correction data is established in the following manner when the gas detector is manufactured.

Figure 6A:
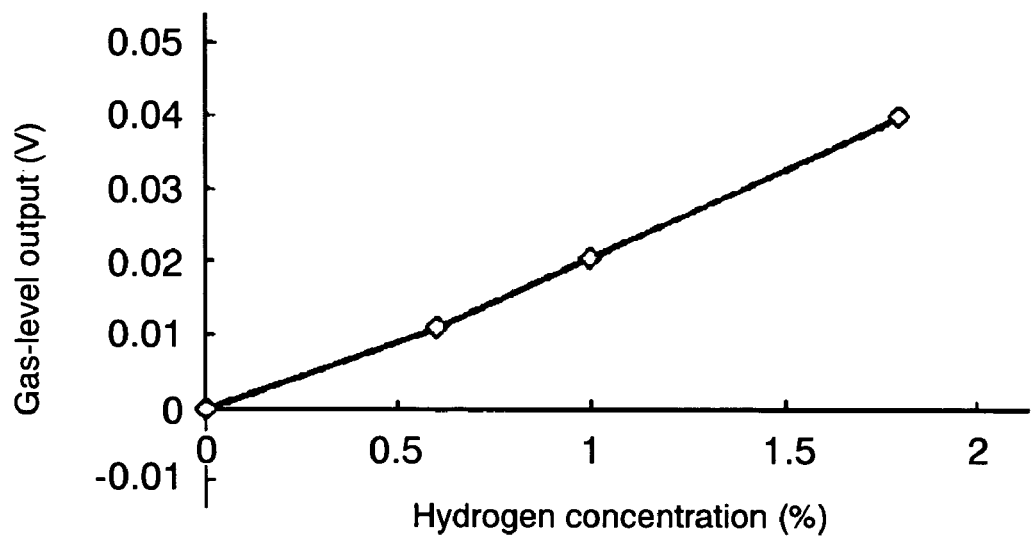
FIGS. 6A and 6B are graphs representing hydrogen concentration and output characteristics under a dry air environment of the gas detector according to the first exemplary embodiment of this invention.
Figure 6B:
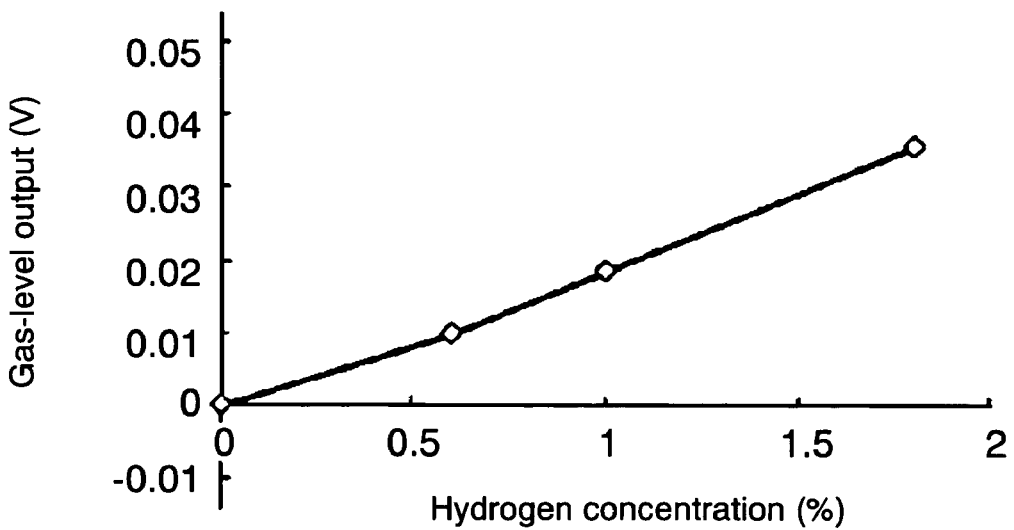

Initially, measurement is made of gas-level outputs for each of DPH 35*a* and DPL 35*b* in relation to changes in hydrogen concentration under the dry air. The measurement is carried out under various temperature conditions. FIG. 6A and FIG. 6B show a result of the measurement under a condition of 80° C. in the ambient temperature. FIG. 6A shows the result of the measurement for DPH 35*a* on a coordinate plane of the hydrogen concentration in the axis of abscissas and the gas-level output in the axis of ordinates. The gas-level output increases in proportion to the hydrogen concentration, as shown in FIG. 6A.

Figure 7:
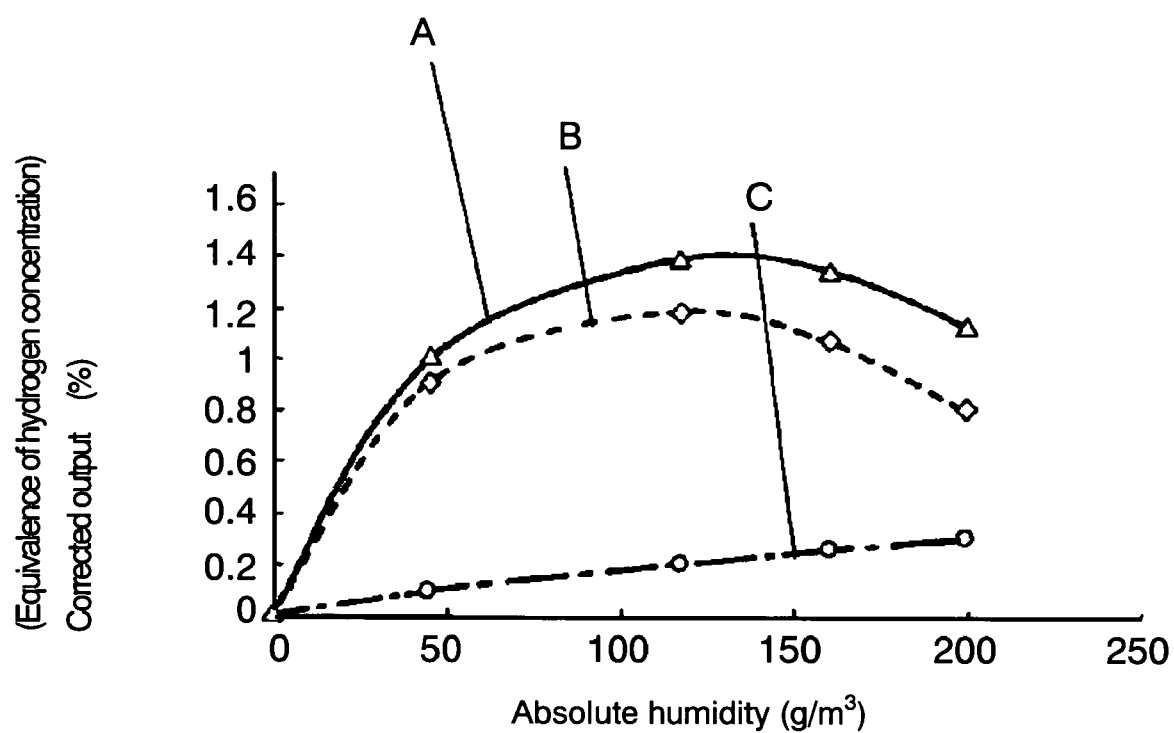
FIG. 7 is a graph representing a humidity and output characteristic of the gas detector according to the first exemplary embodiment of this invention.

Similarly, FIG. 6B shows the result of measurement of the gas-level output of DPL 35*b*. The gas-level output of DPL 35*b* also increases in proportion to the hydrogen concentration. In addition, the voltages across both ends of the individual temperature sensor elements 1*b* and 2*b* of DPH 35*a* and DPL 35*b* are not influenced by the state of the gas to be detected, and they both indicate the ambient temperature. The next step is to obtain relations between the voltage values across both ends of the temperature sensor elements 1*b* and 2*b* and the gas-level outputs of DPH 35*a* and DPL 35*b* respectively. Temperature correction data are then prepared from these data for the sensitivity versus hydrogen concentration. Next, measurement is taken of gas-level outputs from DPH 35*a* and DPL 35*b* while varying humidity in the air. FIG. 7 shows the result of measurement under the condition of 80° C. in the ambient temperature.

The axis of abscissas represents absolute humidity. The axis of ordinates represents the power output converted into hydrogen concentration. This graph exhibits computation of equivalent value to hydrogen concentration after conversion of the humidity-level output into hydrogen concentration. Curve "A" shows the gas-level output of DPH 35*a* corrected based on the idea of temperature correction for the sensitivity to hydrogen, as discussed with reference to FIGS. 6A and 6B, that is, an error margin of the hydrogen detection accuracy (hereinafter referred to as "humidity offset"). Likewise, curve "B" shows humidity offset obtained by correcting the gas-level output of DPL 35*b*. In addition, straight line "C" shows value obtained by subtracting the humidity offset of DPL 35*b* from the humidity offset of DPH 35*a* (referred to as difference "A" hereafter), representing humidity-level output.

It is apparent from FIG. 7 that there is a difference in the humidity offset between DPH 35*a* and DPL 35*b* even though they are under the same absolute humidity condition. This is because the presence of moisture causes a difference in the coefficient of thermal conductivity through water vapor in the vicinity of the individual gas sensor elements 1*a* and 2*a*, of which heating temperatures are different, thereby resulting in the difference of the thermal conductivity between the gas sensor elements 1*a* and 2*a*. It is known from FIG. 7 that the humidity-level output, or difference "A", is proportional to the absolute humidity.

Therefore, by obtaining this humidity-level output, it is possible to make correction of the humidity offset, as well as calculation of the absolute humidity and relative humidity from the condition of the ambient temperature obtained by the temperature sensor elements 1*b* and 2*b*.

Based on these findings, another step is taken to get a relation between the humidity-level output obtained from the difference "A" and the humidity offset, and to prepare humidity correction data and humidity-level output data for detection of the hydrogen concentration.

Figure 8A:
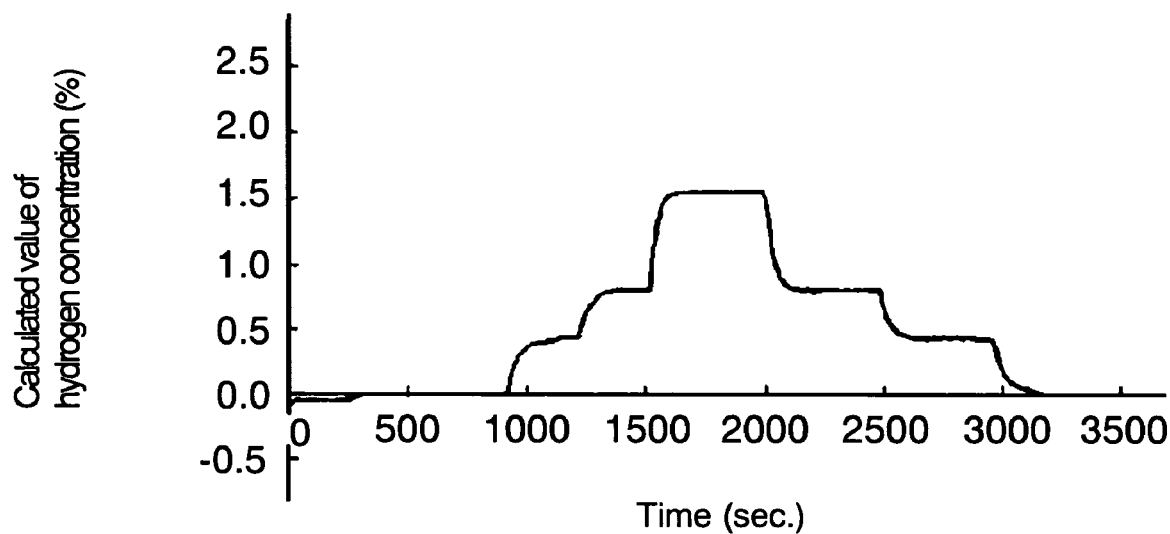
FIGS. 8A and 8B are graphs representing output characteristics after corrective operation of the gas detector according to the first exemplary embodiment of this invention.
Figure 8B:
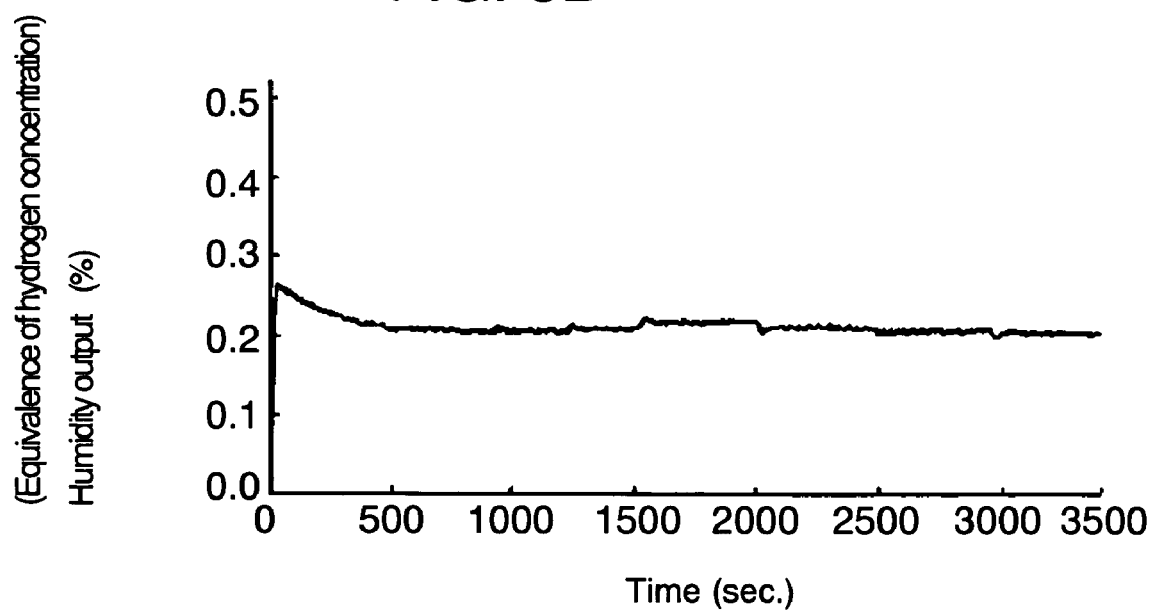

Methods of calculating the above temperature correction for sensitivity to the hydrogen concentration detection and the humidity correction for the humidity-level output and the hydrogen concentration detection are programmed in microcomputer 32. Microcomputer 32 performs the above operations to produce outputs corresponding to the hydrogen concentration and humidity, when it is input with the gas-level output of DPH 35*a*, the gas-level output of DPL 35*b*, and the voltages across both ends of temperature sensor elements 1*b* and 2*b* obtained when the gas detector is in operation. Referring to FIG. 8A and FIG. 8B, description is provided of an example of outputs when the above gas detector is actually operated.

In one example of experiment, air samples having absolute humidity of approximately 120 g/m$^3$ were prepared by mixing them with hydrogen gases to various levels of concentration under the ambient temperature of 80° C., and they were switched one after another in the order of 0%, 0.4%, 0.8%, 1.6%, 0.8%, 0.4%, and 0%. Outputs of the gas detector were then measured after the operation of microcomputer 32. FIG. 8A shows a result of the hydrogen concentration outputs. The axis of abscissas indicates elapsed time during the measurements (in seconds), in which the hydrogen concentration levels were switched in the intervals of 900, 300, 300, 480, 480, 480, 480 seconds. The axis of ordinates indicates calculated value of the hydrogen concentration (%) derived from the gas-level output of DPH 35*a*, the gas-level output of DPL 35*b* and the voltages across both ends of temperature sensor elements 1*b* and 2*b*, by using the above calculation method. Because the curve in this graph representing the hydrogen concentration shows good response to the changes of the gases, it can be verified that the accuracy is also excellent.

FIG. 8B shows a result of the humidity-level outputs. Like FIG. 8A, the axis of abscissas indicates the elapsed time during the measurements (in seconds), and the hydrogen concentration levels were switched in the same intervals as the above measurement of the hydrogen concentration. The axis of ordinates indicates output of absolute humidity-level corresponding to the hydrogen concentration. The humidity-level output shows no variation in FIG. 8B, although the hydrogen concentration level has changed substantially during the measurement, as shown in FIG. 8A. In other words, it is clear that the gas detector accurately outputs only the absolute humidity without being influenced by the changes in the hydrogen concentration. Moreover, this level of the absolute humidity agrees with a reading taken on the gas being measured by humidity measuring instrument in the close vicinity of the gas detector. It is obvious from the above results that the gas detector of the first exemplary embodiment can detect both of the hydrogen concentration and humidity independently with high accuracy.

Another evaluation for detection of hydrogen and humidity was conducted in the like manner as described above, except that GDH 1a and TDH 1b, and GDL 2a and TDL 2b were controlled so that their heating temperatures are maintained at approximately 190° C. and 180° C. respectively. The result showed that the gas detector is still capable of making various corrections, although it lowers the accuracy of output value for the absolute humidity.

The gas detector according to the first exemplary embodiment can be used to compose an apparatus for controlling a fuel cell system and an automobile equipped with it so as to safely shut off hydrogen even if leakage occurs from the system.

(Second Exemplary Embodiment)

In the following second exemplary embodiment, like reference marks are used to designate like elements as those of the first exemplary embodiment, and description of them will be omitted.

A gas detector of this exemplary embodiment differs from that of the first exemplary embodiment in respects that DPH 35a comprises second TDH 1c, and DPL 35b comprises second TDL 2c, in addition to the structure of the first exemplary embodiment.

Figure 9A:
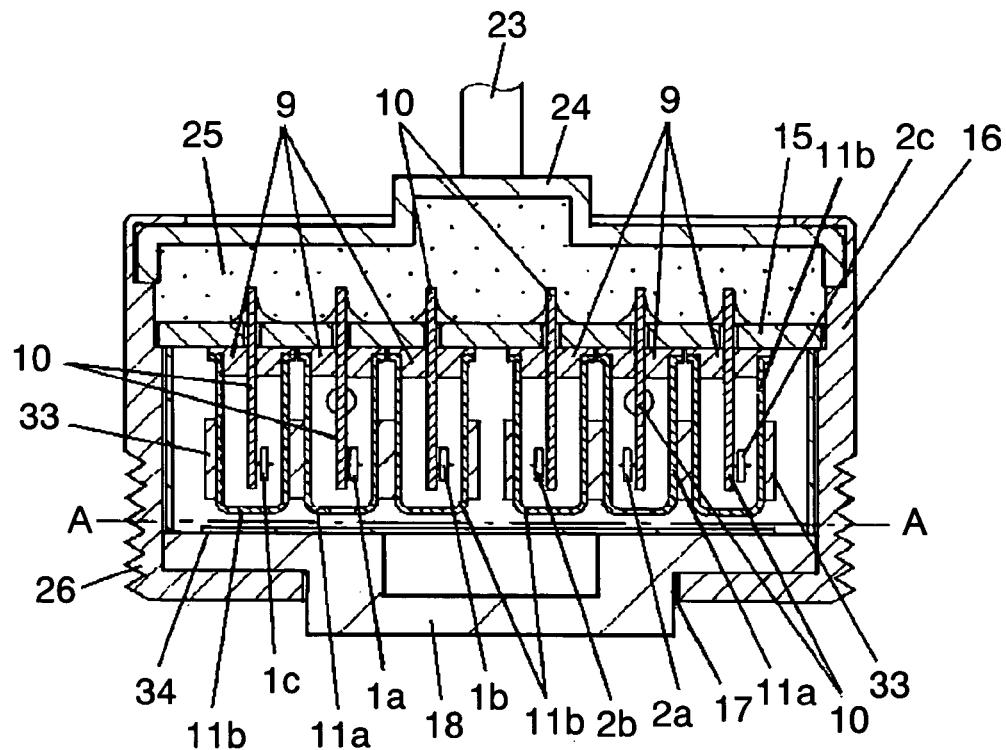
FIG. 9A is a cross sectional view showing a structure of a gas detector according to a second exemplary embodiment of this invention.
Figure 9B:
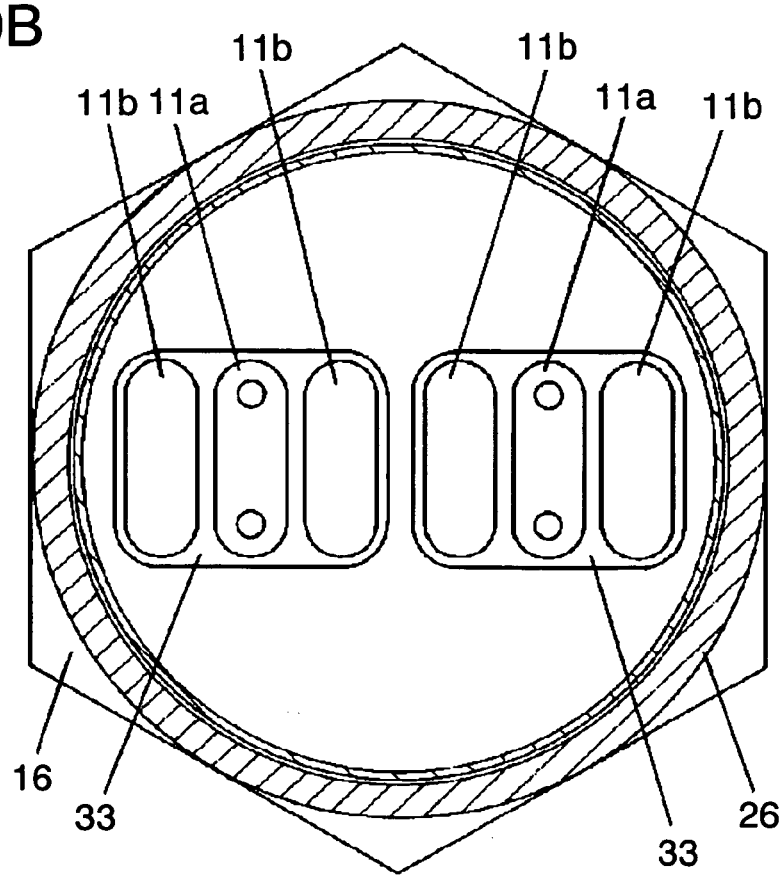
FIG. 9B is a laterally sectioned view taken along a line A—A of the gas detector according to the second exemplary embodiment of this invention.

Description is provided in detail hereinafter. In FIG. 9A and FIG. 9B, second TDH 1c and second TDL 2c are each composed of a thermistor, like those of the first exemplary embodiment. FIG. 2 shows a structure.

The structures of second TDH 1c and second TDL 2c are analogous to the like elements described in the first exemplary embodiment. As shown in FIG. 9A and FIG. 9B, each of the sensor elements is enclosed in unperforated casing 11b in a space filled with dry air, and the unperforated casing 11b and base 9 are bonded and sealed by projection welding. Second TDH 1c and second TDL 2c thus output voltages across their end terminals according to their respective temperatures inside the gas detector without being influenced by the gas to be detected. Accordingly, the gas detector provides an advantage of detecting gas concentration highly accurately in a wide range of temperatures by adopting the above structure in which combinations of the two temperature sensor elements 1b and 2b, and 1c and 2c are placed inside their respective detector units 35a and 35b.

Description is provided next of an operation of the gas detector of this second exemplary embodiment.

Figure 10:
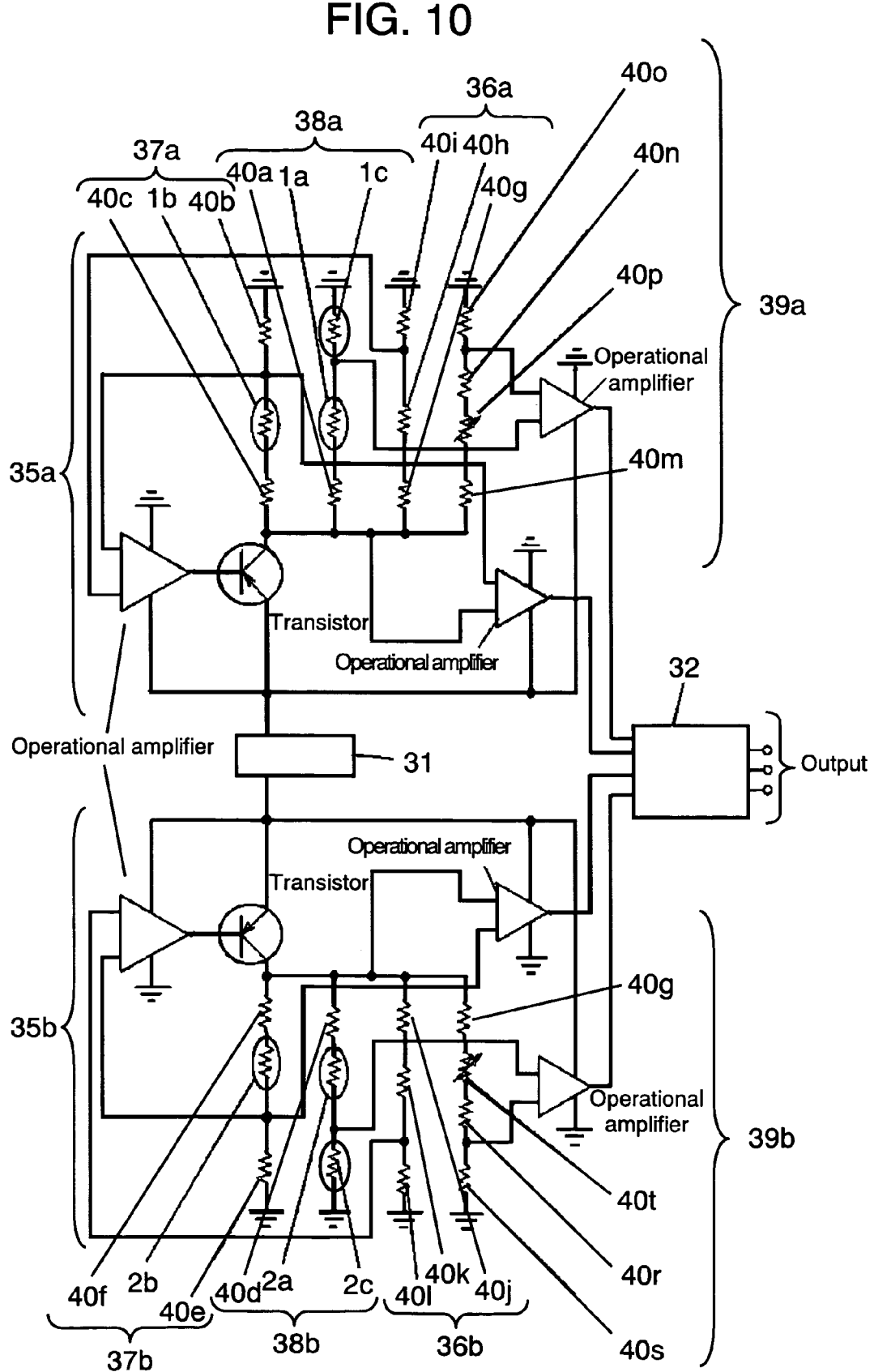
FIG. 10 is a diagram showing a circuit configuration of the gas detector according to the second exemplary embodiment of this invention.

As shown in FIG. 10, GDH 1a, second TDH 1c and fixed resistor 40a of 220 Ω are connected in series to form gas detecting circuit 38a. Fixed resistor 40b of 75 Ω and fixed resistor 40c of 220 Ω are connected to each end of TDH 1b in series thereto, to form ambient temperature detecting circuit 37a.

Similarly, GDL 2a, second TDL 2c and fixed resistor 40d of 500 Ω are connected in series to form gas detecting circuit 38b. Fixed resistor 40e of 320 Ω and fixed resistor 40f of 500 Ω are connected to each end of TDL 2b in series thereto, to form another ambient temperature detecting circuit 37b.

In this embodiment here, heating temperatures of GDH 1a, TDH 1b and second TDH 1c are controlled individually to become approximately 190° C.

In addition, heating temperatures of GDL 2a, TDL 2b and second TDL 2c are controlled individually to become approximately 140° C.

D.C. power source 31 is connected to these circuits and supplies electric power of 15V.

Describing next pertains to a method of controlling the heating temperatures constant. In the second exemplary embodiment, three sensor elements 1a, 1b and 1c of DPH 35a, and another set of three sensor elements 2a, 2b and 2c of DPL 35b are so controlled that their heating temperatures as measured in dry air are kept constant without being influenced by the ambient temperature.

The three sensor elements 1a, 1b and 1c of DPH 35a are controlled in a manner as described hereinafter to make their heating temperatures constant.

Element resistance regulating circuit 36a in DPH 35a consists of fixed resistor 40g of 293 kΩ, fixed resistor 40h of 100 kΩ and another fixed resistor 40i of 100 kΩ connected in series. A voltage across the both ends of fixed resistor 40i serves as a control voltage.

Ambient temperature detecting circuit 37a comprises fixed resistor 40b of 75 Ω and another fixed resistor 40c of 220 Ω connected in series with TDH 1b at each end thereof. A voltage across the both ends of fixed resistor 40b is a to-be-controlled voltage.

Here, a voltage applied to element resistance regulating circuit 36a, gas detecting circuit 38a comprising the series connection of GDH 1a, second TDH 1c and fixed resistor 41a of 220 Ω, reference voltage circuit 39a and ambient temperature detecting circuit 37a is regulated through an operational amplifier, a transistor and the like in response to changes in the ambient temperature, so as to equalize the to-be-controlled voltage with the control voltage. Since the resistances of GDH 1a, TDH 1b and second TDH 1c are kept to be constant at all the time as described above, the heating temperatures of them can be maintained constant.

On the other hand, heating temperatures of three sensor elements 2a, 2b and 2c of the DPL 35b side are controlled constant in the following manner. Element resistance regulating circuit 36b of DPL 35b comprises fixed resistor 40j of 156 kΩ, fixed resistor 40k of 100 kΩ and another fixed resistor 40l of 100 kΩ connected in series. A voltage across the both ends of fixed resistor 40l serves as a control voltage. Ambient temperature detecting circuit 37b comprises fixed resistor 40e of 320 Ω and another fixed resistor 40f of 500 Ω connected in series to TDL 2b at each end thereof. A voltage across the both ends of fixed resistor 40e is a to-be-controlled voltage.

A voltage applied to element resistance regulating circuit 36b, gas detecting circuit 38b comprising the series connection of GDL 2a, second TDL 2c and fixed resistor 40d of 500 Ω, reference voltage circuit 39b and ambient temperature detecting circuit 37b is regulated through an operational amplifier, a transistor and the like in response to changes in the ambient temperature, so as to equalize the to-be-controlled voltage with the control voltage. With the resistances of GDL 2a, TDL 2b and second TDL 2c kept to be constant at all the time as described, the heating temperatures of them can be maintained constant. Since the ambient temperatures of the individual sensor elements are kept generally uniform, they reduce changes in coefficient of thermal conductivity of the gas to be detected due to the effect of temperature. As a result, this embodiment provides the gas detector with such advantages that it can detect gas concentration with high accuracy, and shorten a warm-up time because it controls the self-heating temperatures of the individual sensor elements to be constant immediately after the startup of the gas detector.

Describing next pertains to the steps of signal processing to obtain a gas-level output from each of the detector units 35a and 35b.

In DPH 35a, signal processing is performed in the following manner to obtain a gas-level output. Reference voltage circuit 39a for producing a reference voltage comprises a series connection of fixed resistor 40m of 293 kΩ, fixed resistor 40*n* of a resistance value smaller than 100 kΩ, fixed resistor 40*o* of 100 kΩ, and variable resistor 40*p*. A voltage across both ends of fixed resistor 40*o* is taken as the reference voltage. Gas detecting circuit 38*a* comprises a series connection of GDH 1*a*, second TDH 1*c* and fixed resistor 40*a* of 220 Ω. A voltage across both ends of second TDH 1*c* is a gas-level output voltage. Signal processing is carried out to obtain a difference in voltage potential between the gas-level output voltage and the reference voltage. If there is a difference between the reference voltage and the gas-level output voltage in the air containing no hydrogen and humidity, a resistance of variable resistor 40*p* is adjusted to eliminate the difference.

Signal processing in DPL 35*b* is performed in the following manner to obtain a gas-level output. Reference voltage circuit 39*b* for producing another reference voltage comprises a series connection of fixed resistor 40*q* of 156 kΩ, fixed resistor 40*r* of a resistance value smaller than 100 kΩ, fixed resistor 40*s* of 100 kΩ, and variable resistor 40*t*. A voltage across both ends of fixed resistor 40*s* is used as the reference voltage.

Gas detecting circuit 38*b* comprises GDL 2*a*, second TDL 2*c* and fixed resistor 40*d* of 500 Ω connected in series. A voltage across both ends of second TDL 2*c* is a gas-level output voltage. Signal processing is carried out to obtain another difference in voltage potential between the gas-level output voltage and the reference voltage. If there is a difference between the reference voltage and the gas-level output voltage in the air containing no hydrogen and humidity, a resistance of variable resistor 40*t* is adjusted to eliminate the difference.

Because of the above signal processing, heating characteristics of the individual gas sensor elements 1*a* and 2*a*, and another heating characteristics of the individual second temperature sensor elements 1*c* and 2*c* are made nearly equal in their ratios to a variety of temperatures.

As a result, variations in the gas-level output voltage due to changes of the ambient temperature can be suppressed very low. In the dry air containing no hydrogen and humidity, this embodiment can therefore reduce variations in the potential differences between these reference voltages and gas-level output voltages attributable to the variations of the ambient temperature, and it thus provides an advantage of making highly accurate detection.

Figure 11:
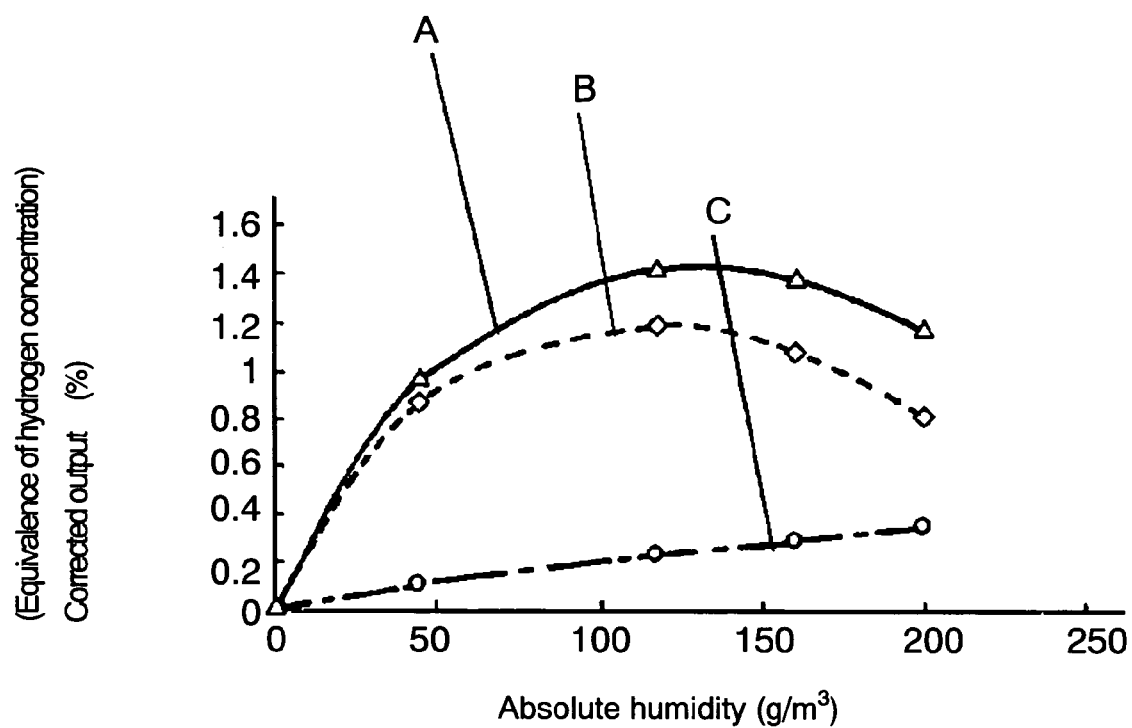
FIG. 11 is a graph representing a humidity and output characteristic of the gas detector according to the second exemplary embodiment of this invention.

The gas-level outputs of DPH 35*a* and DPL 35*b* obtained through the above signal processing, and voltages appearing at both ends of the individual temperature sensor elements 1*b*, 1*c*, 2*b* and 2*c* are input to microcomputer 32. Microcomputer 32 produces outputs corresponding to hydrogen concentration, humidity and temperature respectively by performing an operation similar to that of the first exemplary embodiment. FIG. 11 shows the result of evaluation of the humidity characteristic under the condition of 80° C. in the ambient temperature. The axis of abscissas represents absolute humidity. Curve "A" shows the gas-level output of DPH 35*a* corrected based on the idea of temperature correction for the sensitivity to hydrogen, that is, an error margin of the hydrogen detection accuracy (referred to as "humidity offset"). Likewise, curve "B" shows humidity offset obtained by correcting the gas-level output of DPL 35*b*. In addition, straight line "C" shows value obtained by subtracting the humidity offset of DPL 35*b* from the humidity offset of DPH 35*a* (referred to as difference "B"), representing humidity-level output.

It is apparent from FIG. 11 that there occurs a difference in the humidity offset between DPH 35*a* and DPL 35*b* even though they are under the same absolute humidity condition. This is because the presence of moisture causes a difference in the coefficient of thermal conductivity through water vapor in the vicinity of the individual gas sensor elements, of which heating temperatures are different, thereby resulting in the difference of the thermal conductivity between the gas sensor elements.

The humidity-level output exhibited by the difference "B" is proportional to the absolute humidity, as shown in FIG. 11. Accordingly, since it is proportional to the absolute humidity like that of the first exemplary embodiment, it can be used as a humidity-level output. By obtaining this humidity-level output, it is possible to make correction of the humidity offset as well as calculation of the absolute humidity.

Figure 12A:
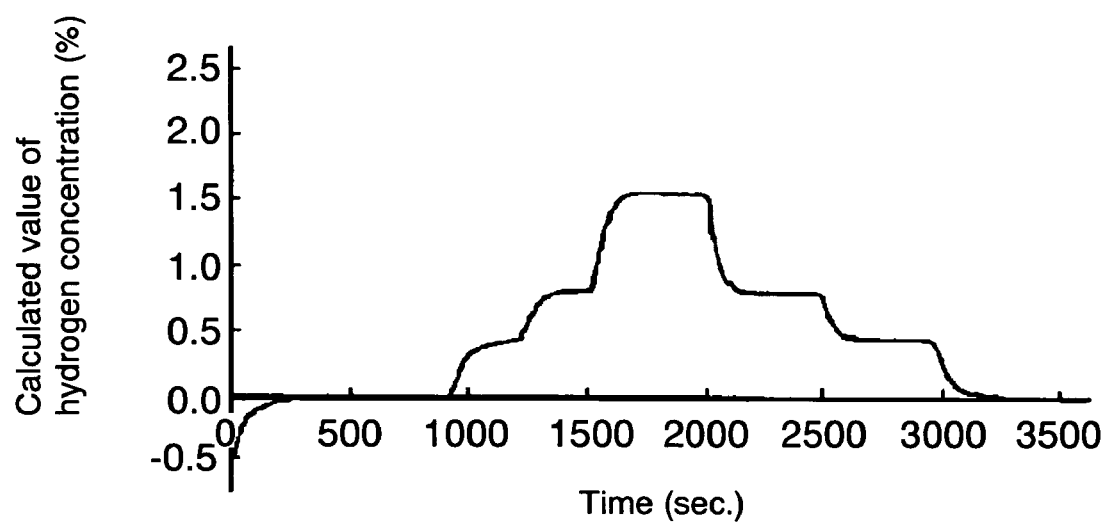
FIGS. 12A and 12B are graphs representing output characteristics after corrective operation of the gas detector according to the second exemplary embodiment of this invention.
Figure 12B:
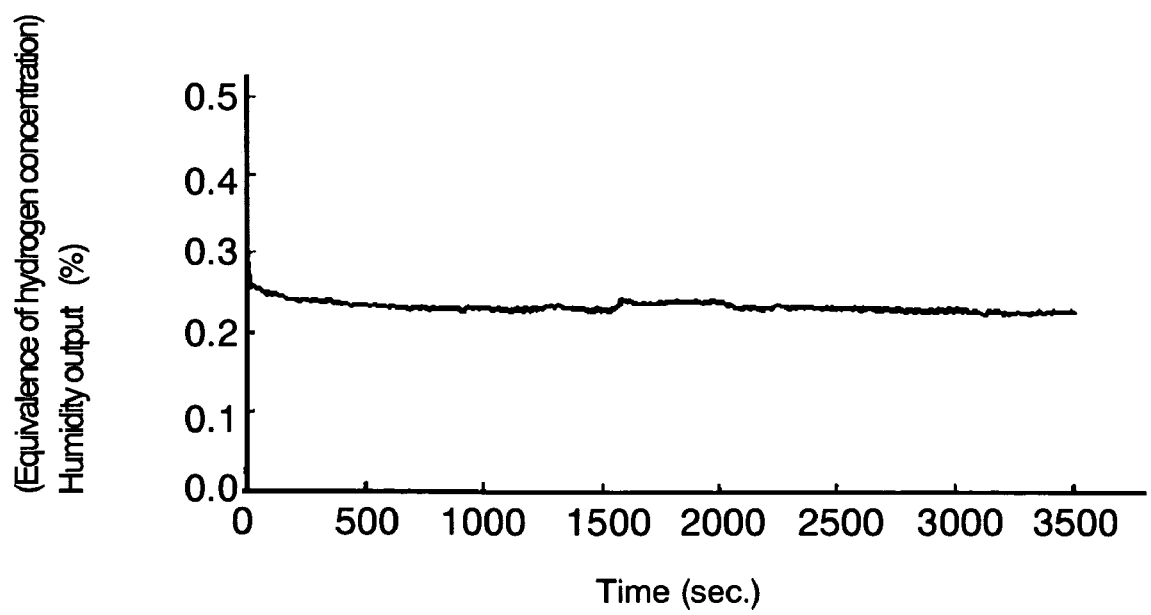

FIG. 12A and FIG. 12B show an example of power outputs of the gas detector according to the second exemplary embodiment. A method of this experiment is identical to that of the first exemplary embodiment.

FIG. 12A shows a result of the hydrogen concentration outputs. The axis of abscissas indicates elapsed time during the measurements (in seconds), in which the hydrogen concentration levels were switched in the intervals of 900, 300, 300, 480, 480, 480, 480 seconds. The axis of ordinates indicates calculated value of the hydrogen concentration (in %) derived from the gas-level output of DPH 35*a*, the gas-level output of DPL 35*b* and any of the voltages across both ends of temperature sensor elements 1*b* and 2*b* and the voltages across both ends of temperature sensor elements 1*c* and 2*c*, by using the above calculation method. Because the curve in this graph representing the hydrogen concentration shows good response to the changes of the gases, it can be verified that the accuracy is also excellent.

FIG. 12B shows a result of the humidity-level outputs. Like FIG. 12A, the axis of abscissas indicates the elapsed time during the measurements (in seconds), and the hydrogen concentration levels were switched in the same intervals as the above measurement of the hydrogen concentration. The axis of ordinates indicates output of absolute humidity-level corresponding to the hydrogen concentration. The humidity-level output shows no variation, although the hydrogen concentration level has changed substantially during the measurement as shown in FIG. 12A. In other words, the gas detector can output only the absolute humidity level accurately without being influenced by the changes of the hydrogen concentration.

In addition, this level of the absolute humidity agrees with a reading taken on the gas being measured by humidity measuring instrument in the close vicinity of the gas detector.

This gas detector can provide a sufficiently high accuracy even when it is used for air conditioning control of a room space in an automobile and the like. According to the above results, it is apparent that the gas detector of the second exemplary embodiment can also detect both the hydrogen concentration and humidity independently with the same high accuracy as that of the first exemplary embodiment.

INDUSTRIAL APPLICABILITY

A gas detector of this invention is adaptable for use in a system for detecting hydrogen leakage from an apparatus used in the normal atmosphere since it can detect hydrogen concentration and humidity independently with respect to each other.

REFERENCE MARKS IN THE DRAWINGS

1a High-temp exothermic gas sensor element
1b High-temp exothermic temperature sensor element
1c Second High-temp exothermic temperature sensor element
2a Low-temp exothermic temperature sensor element
2b Low-temp exothermic temperature sensor element
2c Second Low-temp exothermic temperature sensor element
4 Thermistor element
5 Electrode
6 Lead wire
7 Glass layer
8 Thermistor
9 Base
10 Pin
11a Perforated casing
11b Unperforated casing
15 Circuit board
16 Container
17 Gas intake opening
18 Filter
23 Conductor cable
24 Container cover
25 Moisture resistant resin
26 Screw
27 Pipe
28 Mounting hole
29a–29j, 29l and 29m Fixed resistor
29k, 29n Variable resistor
31 DC power source
32 Microcomputer
33 Heat conductive plate
34 Heater
35a High-temp exothermic detector unit
35b Low-temp exothermic detector unit
36a, 36b Element resistance regulating circuit
37a, 37b Ambient temperature detecting circuit
38a, 38b Gas detecting circuit
39a, 39b Reference voltage circuit
40a–40o, 40q–40s Fixed resistor
40p, 40t Variable resistor

The invention claimed is:

1. A gas detector comprising:
a high-temp exothermic detector unit having a high-temp exothermic gas sensor element and a high-temp exothermic temperature sensor element, each of the sensor elements made of a resistor of which a resistance changes responsive to temperature, the high-temp exothermic gas sensor element exposed to a gas being detected, and the high-temp exothermic temperature sensor element sealed in an unperforated casing filled with dry air and maintained to generate heat to a temperature substantially equal to a self-heating temperature of the high-temp exothermic gas sensor element as measured in dry air; and
a low-temp exothermic detector unit having a low-temp exothermic gas sensor element and a low-temp exothermic temperature sensor element, each of the sensor elements made of a resistor of which a resistance changes responsive to temperature, the low-temp exothermic gas sensor element exposed to the gas being detected, and the low-temp exothermic temperature sensor element sealed in another unperforated casing filled with dry air and maintained to generate heat to a temperature substantially equal to a self-heating temperature of the low-temp exothermic gas sensor element as measured in dry air,
wherein the self-heating temperature of the high-temp exothermic gas sensor element and the high-temp exothermic temperature sensor element of the high-temp exothermic detector unit is set to be different from the self-heating temperature of the low-temp exothermic gas sensor element and the low-temp exothermic temperature sensor element of the low-temp exothermic detector unit as measured in the dry air, and
further wherein the gas detector performs processes of:
converting resistance values of the individual gas sensor elements that change responsive to hydrogen concentration, humidity and an ambient temperature, and resistance values of the individual temperature sensor elements that change responsive to the ambient temperature into electrical gas-level outputs corresponding to the hydrogen concentration and the humidity;
normalizing the gas-level outputs gained from the individual detector units by using a hydrogen sensitivity conversion factor obtained under a known level of hydrogen concentration;
obtaining a humidity-level output derived as a difference between the normalized outputs; and
producing outputs representing levels of the hydrogen concentration and the humidity by correcting the normalized outputs with a humidity-level correction formula established through a correlation of a humidity-level correction value obtained from the humidity-level output gained under an environment of known humidity level and the individual normalized outputs responsive to the humidity.

2. The gas detector as set forth in claim 1, wherein the heating temperatures of the two elements of the low-temp exothermic detector unit and the two elements of the high-temp exothermic detector unit in the dry air are controlled to be constant irrespective of the ambient temperature.

3. The gas detector as set forth in claim 2, wherein:
each of the low-temp exothermic detector unit and the high-temp exothermic detector unit further comprises an element resistance regulating circuit having at least two resistors connected in series for producing a control voltage used for controlling the heating temperatures constant, and an ambient temperature detecting circuit having a resistor connected in series to respective one of the temperature sensor elements for producing a to-be-controlled voltage; and
the method of controlling the heating temperatures of the two sensor elements in each of the low-temp exothermic detector unit and the high-temp exothermic detector unit comprises regulating a voltage applied to the element resistance regulating circuit and the ambient temperature detecting circuit in a manner to equalize the to-be-controlled voltage with the control voltage.

4. The gas detector as set forth in claim 3, wherein:
each of the low-temp exothermic detector unit and the high-temp exothermic detector unit further comprises a reference voltage circuit having at least two resistors and a variable resistor connected in series for producing a reference voltage, and a gas detecting circuit having a resistor connected in series to respective one of the gas sensor elements for producing a gas-level output voltage; and
each of the detector units produces a difference in potential between the reference voltage and the gas-level output voltage as the gas-level output.

5. The gas detector as set forth in claim 1, wherein a temperature-dependent hydrogen sensitivity conversion factor of each of the low-temp exothermic detector unit and the high-temp exothermic detector unit is corrected with a sensitivity correction formula derived from a correlation between the output of the respective one of the temperature sensor elements and the hydrogen sensitivity conversion factor under the environment of various ambient temperatures.

6. The gas detector as set forth in claim 1, wherein:
the high-temp exothermic detector unit further comprises a second high-temp exothermic temperature sensor element made of a resistor of which a resistance changes responsive to temperature, sealed in an unperforated casing filled with dry air and maintained to generate heat to a temperature substantially equal to the self-heating temperature of the high-temp exothermic gas sensor element in dry air;
the low-temp exothermic detector unit further comprises a second low-temp exothermic temperature sensor element made of a resistor of which a resistance changes responsive to temperature, sealed in an unperforated casing filled with dry air and maintained to generate heat to a temperature substantially equal to the self-heating temperature of the low-temp exothermic gas sensor element in dry air; and
the self-heating temperature of the high-temp exothermic gas sensor element, the high-temp exothermic temperature sensor element and the second high-temp exothermic temperature sensor element of the high-temp exothermic detector unit is set to be different from the self-heating temperature in the dry air of the low-temp exothermic gas sensor element, the low-temp exothermic temperature sensor element and the second low-temp exothermic temperature sensor element of the low-temp exothermic detector unit, and
wherein the gas detector performs processes of:
converting resistance values of the individual gas sensor elements that change responsive to hydrogen concentration, humidity and an ambient temperature, and resistance values of the individual temperature sensor elements and the individual second temperature sensor elements that change responsive to the ambient temperature into electrical gas-level outputs corresponding to the hydrogen concentration and the humidity;
normalizing the gas-level outputs gained from the individual detector units by using a hydrogen sensitivity conversion factor obtained under a known level of hydrogen concentration;
obtaining a humidity-level output derived as a difference between the normalized outputs; and
producing outputs representing levels of the hydrogen concentration and the humidity by correcting the normalized outputs with a humidity-level correction formula established through a correlation of a humidity-level correction value obtained from the humidity-level output gained under an environment of known humidity level and the individual normalized outputs responsive to the humidity.

7. The gas detector as set forth in claim 6, wherein the heating temperatures of the three elements of the low-temp exothermic detector unit and the three elements of the high-temp exothermic detector unit in the dry air are controlled to be constant irrespective of the ambient temperature.

8. The gas detector as set forth in claim 7, wherein:
each of the low-temp exothermic detector unit and the high-temp exothermic detector unit further comprises an element resistance regulating circuit having at least two resistors connected in series for producing a control voltage used for controlling the heating temperatures constant, and an ambient temperature detecting circuit having a resistor connected in series to respective one of the temperature sensor elements for producing a to-be-controlled voltage; and
the method of controlling the heating temperatures of the two sensor elements in each of the low-temp exothermic detector unit and the high-temp exothermic detector unit comprises regulating a voltage applied to the element resistance regulating circuit and the ambient temperature detecting circuit in a manner to equalize the to-be-controlled voltage with the control voltage.

9. The gas detector as set forth in claim 8, wherein:
each of the detector units further comprises a reference voltage circuit having at least two resistors and a variable resistor connected in series for producing a reference voltage, and a gas detecting circuit having respective one of the second temperature sensor elements connected in series to respective one of the gas sensor elements for producing a gas-level output voltage; and
each of the detector units produces a difference in potential between the reference voltage and the gas-level output voltage as the gas-level output.

10. The gas detector as set forth in claim 6, wherein a temperature-dependent hydrogen sensitivity conversion factor of each of the detector units is corrected with a sensitivity correction formula derived from a correlation between any of the outputs of the respective ones of the temperature sensor elements and the second temperature sensor elements, and the hydrogen sensitivity conversion factor under the environment of various ambient temperatures.

11. The gas detector as set forth in claim 1, wherein the high-temp exothermic gas sensor element and the low-temp exothermic gas sensor element are individually placed inside perforated casings, and parts of the perforated casings are connected with a heat conductive plate.

12. The gas detector as set forth in claim 1, wherein each of the sensor elements of the low-temp exothermic detector unit and the high-temp exothermic detector unit comprises a thermistor.

13. The gas detector as set forth in claim 1, wherein a difference in the heating temperatures is set to be 10° C. or greater between the individual sensor elements of the low-temp exothermic detector unit and the individual sensor elements of the high-temp exothermic detector unit.

14. The gas detector as set forth in claim 1, wherein the heating temperature of the individual sensor elements of the low-temp exothermic detector unit is set to 100° C. or higher.

15. The gas detector as set forth in claim 1, further comprising a heater disposed in the vicinity of the individual sensor elements of the low-temp exothermic detector unit and the high-temp exothermic detector unit.

* * * * *